United States Patent [19]

Sealfon

[11] Patent Number: 4,698,055

[45] Date of Patent: Oct. 6, 1987

[54] HYPODERMIC SYRINGE

[76] Inventor: Andrew I. Sealfon, 713 North Street, Middletown, N.Y. 10940

[21] Appl. No.: 934,158

[22] Filed: Nov. 24, 1986

[51] Int. Cl.⁴ ............................................. A61M 37/00
[52] U.S. Cl. ......................................... 604/82; 604/92
[58] Field of Search ..................... 604/82, 83, 84, 85, 604/187, 218, 220, 92

[56] References Cited

U.S. PATENT DOCUMENTS

| | | | |
|---|---|---|---|
| 2,541,621 | 2/1951 | Thompson | 604/92 |
| 2,896,622 | 7/1959 | Huttermann | 604/92 |
| 3,889,674 | 6/1975 | Cilento | 604/82 |
| 4,065,360 | 12/1977 | Kreb, III | 604/218 |
| 4,116,240 | 9/1978 | Guiney | 604/92 |

FOREIGN PATENT DOCUMENTS 2154017  5/1973  Fed. Rep. of Germany ...... 604/218

Primary Examiner—John D. Yasko
Attorney, Agent, or Firm—Myron Amer

[57] ABSTRACT

A syringe in which a first medicament is stored in an elongated barrel, adjacent its distal end, while a second medicament is stored in an exterior compartment between the distal and proximal ends in communication with the barrel. A plunger having a piston head with spaced apart sealing rings is located in the syringe barrel with the opposing sealing rings occluding the exterior compartment so as to isolate the medicaments from each other. The piston is normally locked in this position. In use, the piston is moved adjacent the proximal end of the barrel to allow the medicament in the exterior compartment to intermix with the first medicament before dispensing.

3 Claims, 6 Drawing Figures

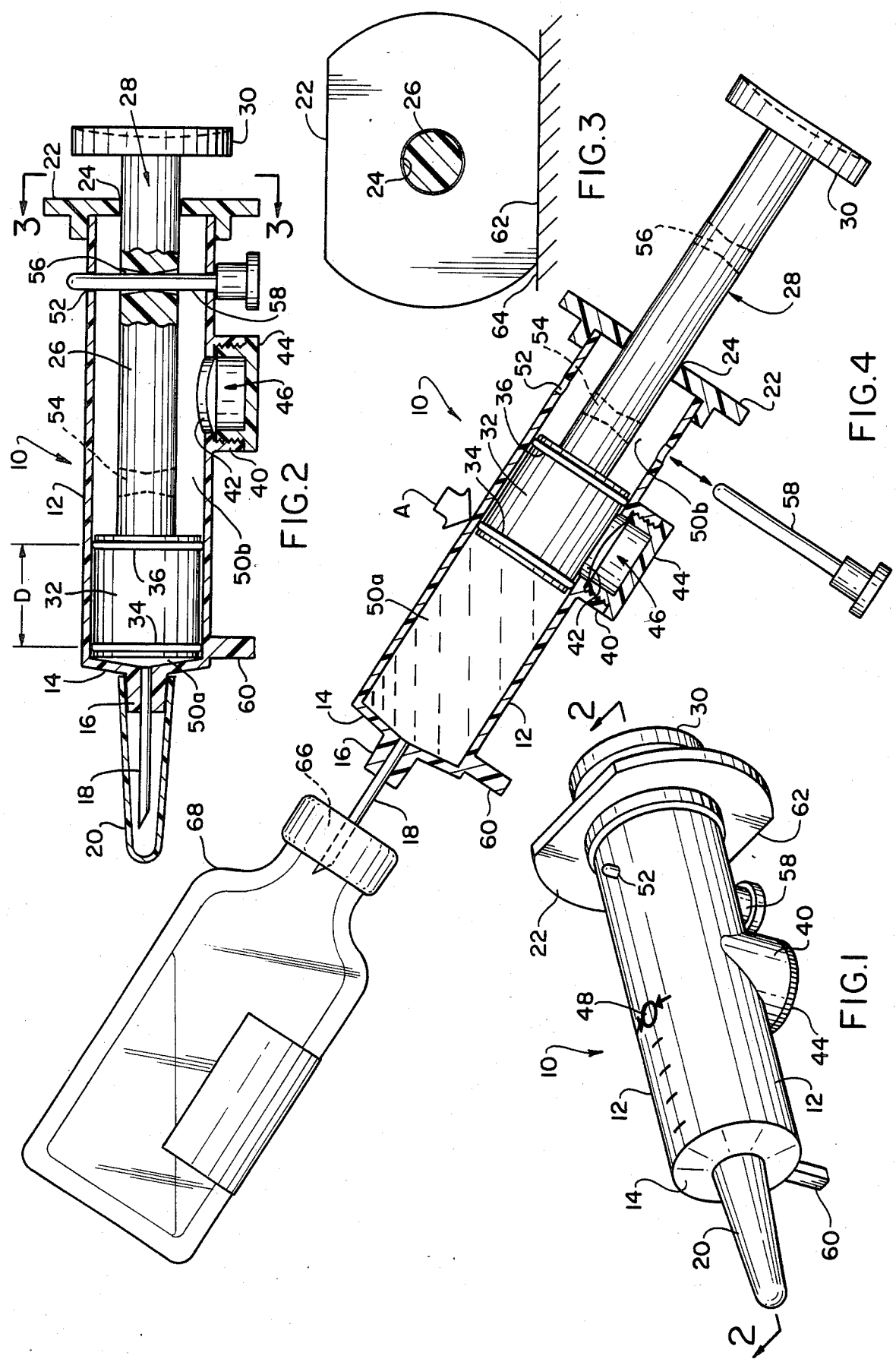

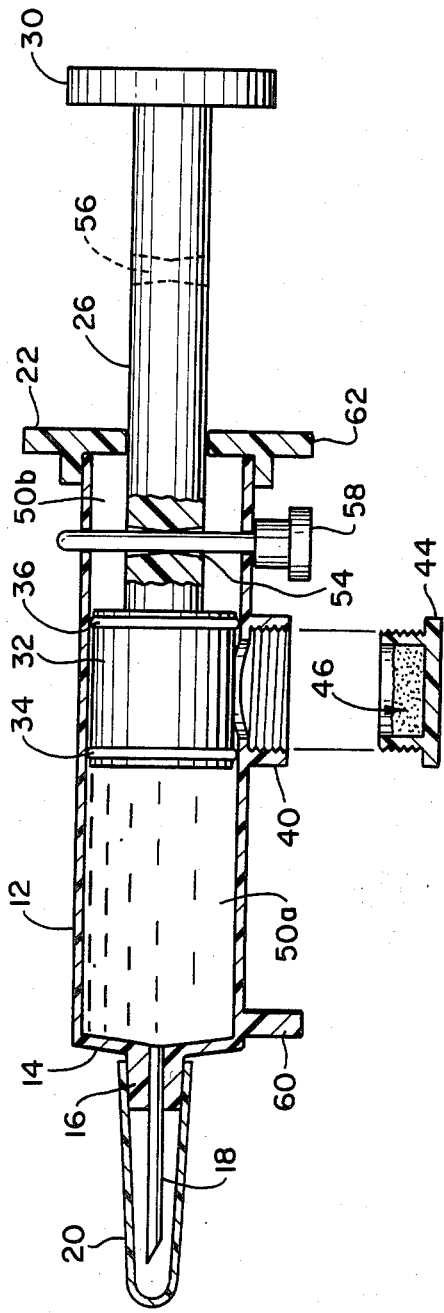
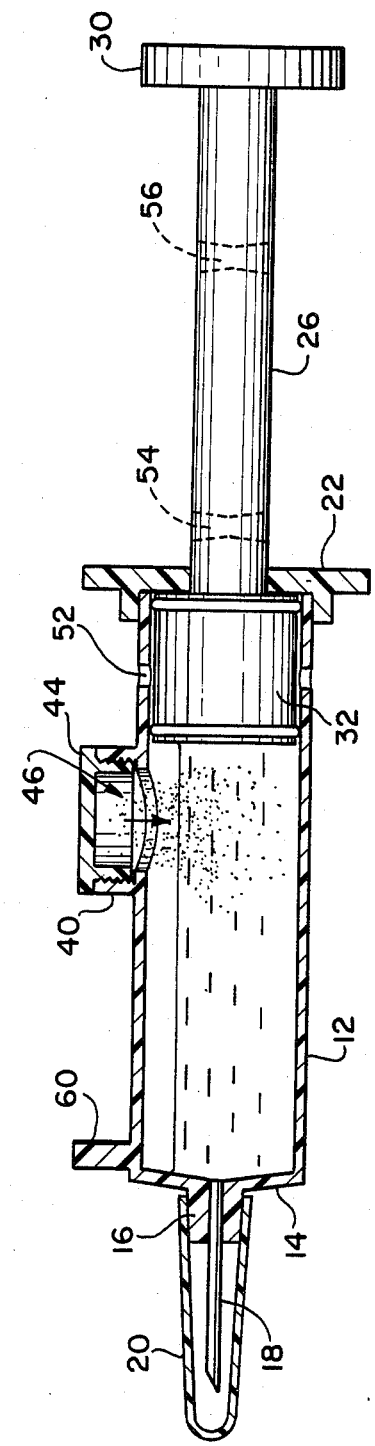
FIG.5
FIG.6

४,६९८,०५५

HYPODERMIC SYRINGE

BACKGROUND OF THE INVENTION

The present invention relates to hypodermic syringes and in particular to a hypodermic syringe for separately storing and mixing small amounts of two medicaments just prior to use.

Many drugs require mixing of powder and liquid immediately before injection into the patient. The constituents are generally separately stored and have to be measured and thereafter mixed prior to insertion into the syringe. Such a multi-step process is not only time consuming, but gives rise to improper measurement of the constituents, as well as to their possible contamination.

In U.S. Pat. No. 3,016,896 a syringe has been proposed in which a powder and liquid may be mixed within the syringe itself. In this patent the syringe is provided with two axially aligned barrel sections, the distal section being normally filled with powder and closed by the forward piston of a two piston plunger. The proximal barrel section is provided with an entrance port through which the liquid constituent of the drug can be eventually inserted as by the use of a second syringe. The forward piston of the plunger is then withdrawn from its seat into the proximal barrel section and the liquid and powder mixed, whereafter the syringe can be used in the conventional manner.

While the syringe suggested in U.S. Pat. 3,016,896 is capable of mixing powder and liquid within the syringe itself, it has several very distinctive disadvantages amongst which are the fact that the liquid and powder must be sequentially loaded into the syringe with the liquid last. The liquid has to be inserted through a hole extending radially into the barrel with the use of a separate syringe and since it is last to be loaded, the syringe itself cannot be used to measure or insure dosage. Further, the syringe must be taken apart completely in order for the powder to be inserted into the axially forward barrel, consequently neither ingredient can be stored in advance within the syringe. Further, dosage accuracy is subject to several errors in that filling the syringe with powder and thereafter with a liquid through a separate syringe can result in spillage, wastage, and thus inaccurate dosing. Still another major disadvantage of the syringe shown in the aforementioned patent is the fact that it cannot be safely filled with each of the constituents and stored for any appreciable length of time without the possibility of leakage between the barrel sections and with depression of the plunger so that premature mixing of the drug may occur during the transport from pharmacy and/or nurse's station to the patient.

It is the object of the present invention to provide a hypodermic syringe which permits stores albeit separately, liquid and powder constituents and permits their mixing just prior to use.

It is another object of the present invention to provide a syringe in which powder and liquid constituents can be stored safely over relatively long periods of time, without fear of mixing, and without fear of premature actuation of the plunger.

It is still a further object of the present invention to provide a hypodermic syringe which is adapted to quickly and easily prepare injectable material in fresh condition immediately prior to the injection thereof into the patient.

It is a further object of the present invention to provide a syringe which has means for storing a medicinal compound in powdered form and means for holding a suitable diluent or solvent for the powder separate from the latter until the same is desired to be mixed and injected into the patient.

The present invention has as a still further object the provision of a hypodermic syringe which is simple in construction and assembly, which is inexpensive to manufacture, and which is quite simple to use.

The foregoing objects together with other objects and further advantages of the present invention are evident from the following disclosure.

SUMMARY OF THE INVENTION

In accordance with the present invention, a first medicament is stored in an elongated syringe barrel, adjacent its distal end while a second medicament is stored in an exterior compartment between the distal and proximal ends in communication with the barrel. A plunger having a piston head with spaced apart sealing rings is located in the syringe barrel, the distal edge of which being normally held in contact with the first medicament, and the opposing sealing rings occluding the exterior compartment so as to isolate the medicaments from each other. In use, the piston is moved adjacent the proximal end of the barrel to allow the medicament in the exterior compartment to intermix with the first medicament. Subsequent movement of the piston towards the distal end dispensing the mixture of the medicaments from the syringe.

The syringe comprises an elongated body bounding a lengthwise chamber between opposite proximal and distal ends and a plunger movable therein. A storage compartment for one of the medicaments is formed on the exterior of the body between the proximal and distal ends of the lengthwise chamber, and is provided with a port communicating with the chamber. The plunger has a piston head dividing the lengthwise chamber into two variable volume sections, and is provided with a pair of seals spaced from each other a distance at least equal to the port from the first storage compartment. The plunger has an initial position of rest wherein the piston head is aligned with the port to occlude the port and defining with the distal end of the chamber, a storage compartment for another medicament, sealed from the exterior storage compartment and from the proximal end of the chamber, and defining with the proximal end of the chamber an area permitting the withdrawal of the piston head. The plunger is movable proximally into the withdrawal area to permit intermixing communication between the medicament storage compartments and thereafter distally to thereby permit the dispensing of the mixture of the medicaments from said syringe.

Full details of the present invention are set forth in the following description and in the accompanying drawings illustrating the present invention.

BRIEF DESCRIPTION OF THE DRAWINGS

FIG. 1 is a perspective view of a hypodermic syringe constructed in accordance with the present invention;

FIG. 2 is a sectional view along line 2—2 of FIG. 1;

FIG. 3 is an end view in the direction of line 3—3 of FIG. 2;

FIG. 4 is a sectional view of the hypodermic needle embodying the present invention showing its loading with the liquid medicament;

FIG. 5 is a medial section view of the syringe according to the present invention showing its loading with the powder medicament; and FIG. 6 is a view similar to that of FIG. 5 showing the act of mixing the powder medicament with the liquid.

DESCRIPTION OF THE INVENTION

As used herein, the term medicament is intended to mean a liquid, powder, or the like intended for injection into a patient whether or not the individual component by itself has medicinal value.

The hypodermic syringe, generally designated by the numeral 10 comprises an elongated substantially hollow cylindrical barrel 12, preferably made of transparent or translucent material. The distal end of the barrel 12 is closed by an end wall 14 from which projects a substantially hollow cylindrical cannula mounting boss 16 in which a hollow needle 18 is securely embedded and over which is force-fit a removable cap 20. The cap 20 is adapted to fit on the boss 16 in sealing engagement, thereby rendering the needle 18 fully enclosed and completely free from contamination.

Mounted at the proximal end of the barrel 12 is a flat finger flange 22 having a central guide hole 24 through which the shaft 26 of a plunger, generally depicted by the numeral 28 passes. In addition to the shaft 26, the plunger 28 is formed at its proximal end with a flange 30, the outer face of which is concave so that the thumb would fit easily. The distal end of the shaft 26 is provided with a cylindrical piston head 32 on which a pair of O-ring piston seals 34 and 36 are axially spaced apart from each other by the distance D. Each of the O-ring seals 34 and 36 slidably engage the inner surface of the barrel 12 and both make constant sealing engagement therewith. The piston head 32 exclusive of the O-rings is only slightly smaller than the inner diameter of the barrel and, therefore, the space between the O-rings 34 and 36 is relatively dead space, wherein no liquid or powder can be stored or transported.

Set back toward the proximal end of the barrel 12 from its mid-point and extending outwardly from its outer surface is an internally threaded boss 40, the barrel 12 being provided with a port 42 opening the boss 40 into the barrel 12. A shallow cylindrical cup 44 is threaded into the boss 40 and defines therewith a side compartment generally identified by the numeral 46. The diameter of the port 42 is slightly less than the distance between the O-ring seals 34 and 36 so that on retraction of the piston head 32, the O-ring seals 34 and 36 can be made to occclude the port 42 (as seen in FIG. 4) therefore sealing against communication between the side compartment 46 and the barrel 12. To be able to ascertain the proper retracted position to occlude the side compartment 46, the barrel 12 is provided with a sighting mark 48 on its surface opposite the distal edge of boss 40 in which the position of the distalmost O-ring 34 can be visible.

It will be observed that when the plunger 28 is retracted, so that the piston head 32 occludes the port 42, the piston head 32 divides the barrel 12 into a distal compartment 50a, defined between the O-ring seal 34 and the end wall 14 and a proximal compartment 50b defined between the O-ring seal 36 and the finger flange 22. In this condition, each of the compartments are isolated not only from each other but from the side compartment 46, and the distal compartment 50a and compartment 46 can be respectively loaded with the different medicament constituents without fear of premature mixture. In this loaded condition, the syringe may be stored and transported preparatory to use.

To insure that the plunger is not prematurely activated during storage or transport, a locking mechanism is provided. To this end the barrel 12 is formed with a diametrically oriented hole 52 between the boss 40 and the finger flange 22 while the plunger shaft 26 is formed with a pair of spaced, transverse through holes 54 and 56 capable of being selectively aligned with the hole 52. A pin 58 is provided to pass through the thus aligned holes locking the plunger 28 against movement relative to the barrel. The distally disposed through hole 54 is spaced from the piston head 32 so that when the distalmost O-ring 34 is aligned at the sighting mark 48 (indicated by the arrow A), the pin 58 is insertable through the barrel 12 and the shaft 26, thus locking the piston head 32 in the loaded position occluding the side chamber 46, as seen in FIG. 4. Similarly, the proximally disposed hole 56 is positioned so that when the plunger 28 is fully depressed, the pin 58 is inserted through it and the barrel 12. This latter condition is employed only during the manufacturing stage and the initial stage of transport from the factory so as to insure against loss or misplacement of the pin 58.

The distal end of the barrel 12 is provided with a depending leg 60, while the proximal end of the finger flange 22 is cut back along a chord 62 parallel to the edge of the leg 60. The leg 60 and the chord 62 lie in a plane also containing the outer surface of the cup 44 so that syringe 10 may be stably set upon a horizontal surface 64 such as a table or tray. Thus, the syringe may be easily carried on a tray while maintaining the syringe 10 otherwise free from contact with any possibly contaminating surface. Lastly, the outer surface of the barrel may be provided with several lines or other indicia indicating the corresponding volumes within the barrel 12.

The syringe 10 of the present invention is normally manufactured and packaged without any medicament stored therein. In this condition, the plunger 28 is fully depressed so that the piston head 32 lies fully adjacent the distal end wall 14 and the locking pin 58 is inserted into the proximal transverse hole 56, the cup 44 being threaded onto the boss 40 previously. The entire unit is then preferably packaged in a heat seal plastic bag and shipped from factory to doctor or hospital.

To prepare the syringe 10 for use, it is, of course, removed from the plastic bag and the plunger 28 is also freed from its factory condition by removing the pin 58. The syringe is then filled with the liquid by inserting the needle 18, in conventional manner through the rubber stopper 66 of liquid storage vial 68 and the plunger 28 is withdrawn, drawing into the distal compartment 50a of the barrel 12 a measured amount of the liquid from the vial 68. When the selected amount of liquid is introduced into the barrel 12, the needle is withdrawn from the vial 68, and the plunger 28 continued to the position, wherein its head 32 closes the port 42 from the side compartment 46. At this point, the pin 58 is reinserted into the barrel 12, through the distal transverse hole 54, thereby again locking the plunger 28 against any movement. In this normal rest condition, the shield 20 is replaced onto the cannula boss 16. Thereafter, the cup 44 is unscrewed, filled with the powdered medicament and replaced, loading the side chamber 46 with the necessary medicament as seen in FIG. 5. In this condition, the syringe 10 is fully loaded with both liquid and powdered constituents, which are otherwise permanently isolated from each other because the locking pin 58 prevents depression or retraction of the plunger 28 which would cause the two compartments 50a and 46 to be in communication. The syringe 10 may thus be returned to an antiseptic package, stored and/or transported to the patient for further use.

Just prior to injecting the patient, the pin 58 is removed, freeing the plunger 28 which is then fully retracted into the proximal compartment 50b beyond the side compartment 46 allowing the liquid and the powder to mix together, as seen in FIG. 6. Once the mixture is fully agitated and homogeneously mixed, the plunger 28 is pushed forwardly, while the syringe 10 is rotated upside down, to insure that all of the mixed medication falls into the distal compartment 50a, and while the side compartment 46 is on top, the plunger 28 is again depressed until the piston head 32 again occludes the side compartment 46. At this point the patient may be injected with the mixture, or the syringe further stored for later use by returning the pin 58 into the hole 52 of the barrel 12. Since the needle and syringe are otherwise comparable to the standard or known syringes currently in use, actual injection in the patient follows customary usage. Preferably, once injection is completed, the syringe may be destroyed or sterilized and reused.

Various embodiments and modifications have been suggested in the foregoing disclosure, others will be apparent to those skilled in the art. Accordingly, it is intended that the present disclosure be taken as illustrative only, and not limiting the scope of the invention.

What is claimed is:

1. A hypodermic syringe comprising a barrel having proximal and distal ends, a plunger extending outwardly of the proximal end and movably disposed within said barrel to divide said barrel into a pair of variable volume comprising and a fixed storage compartment located on the exterior of said barrel and having an opening in communication with the interior of said barrel at a selected point midway between the distal and proximal ends of said barrel, said plunger having a piston head on which is disposed a pair of seals spaced apart a distance at least equal to the opening from said fixed volume storage compartment, said plunger being positionable during its movement in said barrel to place said piston head straddling the opening from said fixed volume compartment to sealingly isolate said fixed volume compartment from said variable volume compartments, and a pin passing simultaneous through a hole in said barrel and said plunger proximaly of said piston head for releaseably locking said plunger against movement relative to said barrel at least in said straddling position.

2. The hypodermic syringe according to claim 1, wherein said fixed volume compartment comprises a cylindrical boss extending laterally from said barrel and a cup-shaped cap removably threaded to said boss.

3. The hypodermic syringe according to claim 1, including indicia on the exterior of said barrel indicating the position of said piston head straddling the opening to the fixed volume compartment.

* * * * *